United States Patent [19]

Nakagawa et al.

[11] Patent Number: 4,971,799
[45] Date of Patent: Nov. 20, 1990

[54] PERCUTANEOUS-ADMINISTRATION-TYPE PHARMACEUTICAL PREPARATION OF NITROGLYCERIN

[75] Inventors: Takashi Nakagawa, Otsu; Masayasu Kurono, Mie; Makoto Sato, Aichi; Tsutomu Ishida, Iwakura; Kazushi Tokita, Aichi; Katsuhiko Takahashi, Aichi; Masato Azuma; Satoshi Uenoyama, both Osaka, Japan

[73] Assignees: Sekisui Kagaku Kogyo Kabushiki Kaisha, Osaka; Sanwa Kagaku Kenkyusho Co., Ltd., Nagoya; Nippon Oil & Fats Co., Ltd., Tokyo, all of Japan

[21] Appl. No.: 175,820

[22] Filed: Mar. 31, 1988

[30] Foreign Application Priority Data

Mar. 31, 1987 [JP] Japan ................................. 62-80817

[51] Int. Cl.$^5$ .............................................. A61F 13/02
[52] U.S. Cl. ...................................... 424/448; 424/443
[58] Field of Search ................. 424/447, 448, 449, 443

[56] References Cited

U.S. PATENT DOCUMENTS

| | | | |
|---|---|---|---|
| 4,286,592 | 9/1981 | Chandrasekaran | 128/260 |
| 4,291,015 | 9/1981 | Keith et al. | 424/80 |
| 4,336,243 | 6/1982 | Sanvordeker et al. | 128/260 |
| 4,421,737 | 12/1983 | Ito et al. | 424/448 X |
| 4,466,953 | 8/1984 | Keith et al. | 424/80 |
| 4,470,962 | 9/1984 | Keith et al. | 424/80 |
| 4,505,891 | 3/1985 | Ito | 424/449 |
| 4,608,249 | 8/1986 | Otsuka et al. | 424/80 |
| 4,615,699 | 10/1986 | Gale et al. | 424/448 |
| 4,751,087 | 6/1988 | Wick | 424/448 X |
| 4,769,028 | 9/1988 | Hoffman et al. | 424/443 |
| 4,814,168 | 3/1989 | Sablotsky et al. | 424/448 |

FOREIGN PATENT DOCUMENTS

| | | |
|---|---|---|
| 0035399 | 9/1981 | European Pat. Off. . |
| 0062682 | 10/1982 | European Pat. Off. . |
| 0156080 | 10/1985 | European Pat. Off. . |
| 0181970 | 5/1986 | European Pat. Off. . |
| 54-16566 | 2/1979 | Japan . |
| 55-2604 | 1/1980 | Japan . |
| 0056424 | 4/1982 | Japan ................................. 424/447 |
| 8606281 | 11/1986 | World Int. Prop. O. . |

OTHER PUBLICATIONS

WO 8201317, 4/82 from 424/448.
Patent Abstracts of Japan, vol. 7, No. 155 (C-175) [1300], Jul. 7th, 1983; & JP-A-58 67 776 (Sekisui Kagaku Kogyo K.K.) 22-04-1983.
Patent Abstracts of Japan, vol. 6, No. 154 (C-119) [1032], Aug. 14th 1982; & JP-A-57 75 917 (Nichiban K.K.) 12-05-1982.
Patent Abstracts of Japan, vol. 8, No. 11 (C-205) [1448], Jan. 18th 1984; & JP-A-58 177 913 (Sekisui Kagaku Kogyo K.K.) 18-10-1983.

Primary Examiner—Thurman K. Page
Attorney, Agent, or Firm—Irell & Manella

[57] ABSTRACT

A percutaneous-administration-type pharmaceutical preparation of nitroglycerin comprising a backing that is impervious to medicines, and a pressure-sensitive adhesive layer that is disposed on one surface of the backing, wherein the pressure-sensitive adhesive layer contains alkyl (meth)acrylate copolymer in the concentration of 80-95% by weight and the nitroglycerin in the concentration of 5-20% by weight, said copolymer contains as major copolymer components alkyl (meth)acrylate with alkyl groups having 6 or more carbon atoms, which alkyl (meth)acrylates include 2-ethylhexylmethacrylate in the concentration of 40-90% by weight based on the total weight of said alkyl (meth)acrylates, and the copolymer has a rolling ball tack value of 2 or less. The preparation obtained makes it possible for nitroglycerin to be absorbed percutaneously at a controlled rate for long periods of time.

6 Claims, No Drawings

PERCUTANEOUS-ADMINISTRATION-TYPE PHARMACEUTICAL PREPARATION OF NITROGLYCERIN

BACKGROUND OF THE INVENTION

1. Field of the Invention:

This invention relates to a pharmaceutical preparation in pressure-sensitive adhesive tape form that permits the percutaneous absorption of nitroglycerin over a long period of time at a controlled rate.

2. Description of the Prior Art:

Nitroglycerin is used as a medicine for the treatment and for the prevention of heart disease such as angina pectoris, myocardial infarction, cardiac insufficiency, and the like. When nitroglycerin is administered by, for example, intravenous injection, its effects are lost after a very short period of time. Also, because the nitroglycerin in the blood is thereby raised to a high level for a short period of time, there are the disadvantages of side effects such as headache, dizziness, orthostatic hypotension, etc. In order to keep the blood level of nitroglycerin at a fixed value for relatively long periods of time, a preparation that has a layer of adhesive that contains nitroglycerin on a backing can be used, and the nitroglycerin can be absorbed percutaneously. The drug nitroglycerin is relatively easily absorbed through the skin. For that reason, if adhesives such as natural rubber, silicone resin, etc., in which nitroglycerin is relatively insoluble are used, the skin adhesive partition coefficient of nitroglycerin is high, and the permeation rate through the skin is therefore too high, resulting in the side effects mentioned above. In order to achieve the effective use of the pharmacological effects of nitroglycerin, continuous percutaneous absorption by which the blood level of nitroglycerin of 0.05–2.0 ng/ml is maintained is preferable. For this purpose, a number of steps have been taken, such as the selection of a base by which the rate of percutaneous absorption of the nitroglycerin can be controlled.

Preparations that contain nitroglycerin have been disclosed in, for example, Japanese Laid-Open Patent Publication Nos. 56-133381, 57-77617, and 55-2604. All of these preparations make use of bases that can control the release of nitroglycerin more readily than with bases such as those mentioned above, including natural rubber, polyisobutylene, etc. For example, the preparation disclosed in Japanese Laid-Open Patent Publication No. 57-77617 has a copolymer as the adhesive base that can be obtained by the copolymerization of dodecyl methacrylate, a functional monomer such as acrylic acid, and a specific alkyl (meth)acrylate. However, when this kind of preparation is made by the ordinary method for the application using solvents, the solvent and the nitroglycerin volatilizes together when the solvent is removed or at the time of drying, because the compatibility of the nitroglycerin and the adhesive base material is low. Nitroglycerin is explosive, so a large amount of volatilized nitroglycerin is extremely dangerous during manufacture. There has been an impregnation method by which the above-mentioned preparation can be produced without any danger. In this method, first, an adhesive layer that does not contain any drug is formed on top of the backing, and a soft ointment or the like that contains nitroglycerin is applied to this adhesive layer and left to mature so that nitroglycerin is transferred to the adhesive layer. However, it is difficult by use of this impregnation method to achieve an adhesive base in which the nitroglycerin is distributed uniformly at a high concentration. In this way, the preparation that can be obtained by the impregnation method has a small amount of nitroglycerin in the adhesive base, so pharmacological effectiveness over long periods of time is not achieved. Moreover, per unit of surface area, the amount of nitroglycerin is small, so it is necessary to use a large surface area of the preparation in order to achieve the percutaneous absorption of a fixed amount of nitroglycerin.

Preparations that attain transdermal-controlled administration of nitroglycerin without selection of the variety of the adhesive base material have been proposed by, for example, Japanese Patent Publication No. 54-16566, in which a layer of base material that contains a high concentration of nitroglycerin is formed on a backing, and on this layer, a membrane (i.e. a controlled release membrane) that has micropores and then an adhesive layer are placed in that order to form the preparation. Japanese Laid-Open Patent Publication Nos. 55-94316, 57-14522, 57-500831, and 57-59806 disclose a preparation that is composed of two separate parts, a base layer of non-adhesive resin such as polyvinyl alcohol containing nitroglycerin therein and an adhesive layer by which this base material that contains nitroglycerin is made to adhere to the skin surface. Japanese Laid-Open Patent Publication Nos. 59-207149 and 56-125311 disclose preparations in which a plurality of base layers that contain different concentrations of nitroglycerin are disposed on a backing, and an adhesive layer is disposed thereon. A preparation has been proposed in which the adhesive layer contains nitroglycerin that has been microencapsulated in a micro-pore film. However, the manufacture of all of these preparations is complicated, which makes difficulties in obtaining a preparation that contains nitroglycerin at low cost.

SUMMARY OF THE INVENTION

The percutaneous-administration-type pharmaceutical preparation of this invention, which overcomes the above-discussed and numerous other disadvantages and deficiencies of the prior art, comprises a percutaneous-administration-type pharmaceutical preparation of nitroglycerin comprising a backing that is impervious to medicines, and a pressure-sensitive adhesive layer that contains alkyl (meth)acrylate copolymer and nitroglycerin, said pressure-sensitive adhesive layer being disposed on one surface of said backing, wherein said pressure-sensitive adhesive layer contains the copolymer in the concentration of 80–95% by weight and the nitroglycerin in the concentration of 5–20% by weight, the number of carbons in the alkyl groups of the alkyl (meth)acrylate that forms said copolymer is 6 or more, said copolymer contains 2-ethylhexylmethacrylate as a copolymer component in the concentration of 40–90% by weight, and said copolymer has a rolling ball tack value of 2 or less.

In a preferred embodiment, the alkyl (meth)acrylate copolymer contains poly-functional monomers as copolymer components in the concentration of 0.001–0.1% by weight based on the total weight of all monomers of said copolymer.

In a preferred embodiment, the alkyl (meth)acrylate copolymer consists essentially of alkyl (meth)acrylates with alkyl groups having 6 or more carbon atoms.

The method for the manufacture of percutaneous-administration-type pharmaceutical preparations of nitroglycerin of this invention comprises applying an organic-solvent solution that contains alkyl (meth)acrylate copolymer and nitroglycerin to one surface of a backing that is impervious to medicines; and drying said coated layer on the backing, resulting in a pressure-sensitive adhesive layer, wherein said copolymer contains alkyl (meth)acrylates as copolymer components, which alkyl (meth)acrylates include 2-ethylhexylmethacrylate in the concentration of 40–90% by weight based on the total weight of said alkyl (meth)acrylates, and has a rolling ball tack value of 2 or less, said organic solvent has a solubility parameter of 8.9–9.9, and said pressure-sensitive adhesive layer contains said copolymer in the concentration of 80–95% by weight and said nitroglycerin in the concentration of 5–20% by weight.

In a preferred embodiment, the alkyl (meth)acrylate copolymer contains poly-functional monomers as copolymer components in the concentration of 0.001–0.1% by weight based on the total weight of all monomers of said copolymer.

In a preferred embodiment, the alkyl (meth)acrylate copolymer consists essentially of alkyl (meth)acrylates with alkyl groups having 6 or more carbon atoms.

Thus, the invention disclosed herein makes possible the objectives of (1) providing a percutaneous-administration-type pharmaceutical preparation of nitroglycerin with which the level of nitroglycerin in the blood can be maintained at a fixed level for, for example, 24 hours or more, at a controlled rate of absorption; (2) providing a percutaneous-administration-type pharmaceutical preparation of nitroglycerin with which a satisfactory pharmacological effect can be obtained with a small surface area, and because the surface area is small, the feeling of discomfort by the application of the preparation is reduced; (3) providing a percutaneous-administration-type pharmaceutical preparation of nitroglycerin with excellent pressure-sensitive adhesive qualities, which will adhere to the surface of the skin for long periods of time; (4) providing a percutaneous-administration-type pharmaceutical preparation of nitroglycerin with a simple structure, with a single pressure-sensitive adhesive layer on a backing; (5) providing a percutaneous-administration-type pharmaceutical preparation of nitroglycerin that contains a precise amount of nitroglycerin; and (6) providing a method for the manufacture of the above-mentioned preparation in which there is no danger during the manufacturing process and which is produced at low cost.

DESCRIPTION OF THE PREFERRED EMBODIMENTS

In the percutaneous-administration-type pharmaceutical preparation of nitroglycerin of this invention, alkyl (meth)acrylate copolymer is used as the base material. Alkyl (meth)acrylates which are the copolymerization ingredients of this alkyl (meth)acrylate copolymer, has alkyl groups with 6 or more carbons. As this kind of alkyl (meth)acrylate, there are 2-ethylhexyl (meth)acrylate, hexyl (meth)acrylate, heptyl (meth)acrylate, octyl (meth)acrylate dodecyl (meth)acrylate, lauryl (meth)acrylate, stearyl (meth)acrylate, etc. Copolymer made from these kinds of alkyl (meth)acrylate is saturated by about 20% by weight or less of nitroglycerin. If the carbon number of the alkyl groups mentioned above is less than 6, the amount of nitroglycerin needed for saturation increases (to more than 20% by weight). The affinity of this kind of copolymer for nitroglycerin is very great, so the skin adhesive partition coefficient of nitroglycerin is small, and the percutaneous absorption Moreover, 40–90% by weight of the alkyl (meth)acrylate that forms the copolymer, and preferably 60–80% by weight, is 2-ethylhexylmethacrylate. In this way, when the carbon number of the alkyl groups of the alkyl (meth)acrylate that constitutes a copolymer is 6 or more, and the copolymer contains 2-ethylhexylmethacrylate in the range mentioned above, the copolymer is saturated by about 10–20% by weight of nitroglycerin. When nitroglycerin is mixed with this kind of copolymer, the copolymer will have a suitable degree of polarity, and also, because the affinity of the nitroglycerin to the said copolymer is suitable, the nitroglycerin can be absorbed percutaneously at a fixed rate over long periods of time. If the amount of 2-ethylhexylmethacrylate in the copolymer is less than 40% by weight, the pressure-sensitive adhesive layer will be softened excessively when nitroglycerin is present in high concentrations. For that reason, the cohesive strength of the pressure-sensitive adhesive layer will be insufficient, and when the preparation is peeled off of the surface of the skin, the adhesive material will remain on the skin. Since the adhesive strength of such copolymer is great, the removal of the preparation may cause pain. If the amount of 2-ethylhexylmethacrylate in the copolymer is more than 90% by weight, the pressure-sensitive adhesive layer will be hardened, and the adhesive strength of the preparation will decrease, so that it will be too readily removed from the skin during use. The two more monomers that contain the 2-ethylhexylmethacrylate mentioned above are chosen so that the copolymer obtained from the said monomers will have a rolling ball tack value of 2 or less.

When needed, a trace amount of radical polymerizable poly-functional monomer can be included as a copolymer component in the copolymer mentioned above. This poly-functional monomer has two or more radical polymerizable groups such as a vinyl group, allyl group, etc., per molecule of the said monomer. For example, there are divinylbenzene, methylene bisacrylamide, ethleneglycol di(meth)acrylate, propyleneglycol di(meth)acrylate, butyleneglycol di(meth)acrylate, hexyleneglycol di(meth)acrylate, polyethyleneglycol di(meth)acrylate, polypropyleneglycol di(meth)acrylate and trimethylolpropane tri(meth)acrylate. When these poly-functional monomers are added at the time of copolymerization, cross-linkage slightly arises in the copolymer, so the cohesion of the adhesive base material finally obtained is excellent, and when the pharmaceutical preparation of nitroglycerin is removed from the skin, the pressure-sensitive adhesive layer does not remain on the skin surface. The poly-functional monomers are used in a concentration of 0.1% by weight or less of the total monomers that form the copolymer, and ordinarily 0.01–0.1% by weight. If more than 0.1% by weight is used, there is gelation at the time of polymerization, and a uniform solution cannot be obtained.

The copolymer can be prepared by the solution-polymerization method (radical polymerization) or the like. For example, two or more kinds of alkyl (meth)acrylate including the 2-ethylhexylmethacrylate mentioned above and a poly-functional monomer as needed are placed in a reaction vessel together with solvent and allowed to polymerize under a nitrogen atmosphere at 60°–100° C. while being agitated with a peroxide, etc., as catalyst. The copolymer obtained in this way, with a rolling ball tack value of 2 or less, is not in itself pressure-sensitive adhesive. However, when nitroglycerin is added to this copolymer, the plasticization effect of the nitroglycerin causes the development of an appropriate degree of pressure-sensitive adhesiveness.

When acryl-type pressure-sensitive adhesives are used ordinarily in percutaneous-administration-type pharmaceutical preparations, in order to ensure an appropriate cohesiveness, methods such as (1) a method for the manufacture of pressure-sensitive adhesive in which monomers that have polar groups such as carboxyl groups, hydroxyl groups, amide groups, or the like are used as a component of the copolymer, and (2) a method by which after the formation of the pressure-sensitive adhesive layer, polymers contained in the pressure-sensitive adhesive layer are cross-linked by the use of metal ions, isocyanate compounds, epoxy compounds, peroxides, etc., or by irradiation of an electron beam, have been used. In this invention, as described above, a copolymer that has a specific composition with a rolling ball tack value of 2 or less is used. In a system in which this kind of copolymer and nitroglycerin are uniformly mixed together, at the same time as the development of pressure-sensitive adhesiveness, satisfactory cohesiveness is also achieved. Therefore, it is possible to ensure a high degree of cohesiveness without use of the conventional methods mentioned above to raise the cohesive strength. With the use of method 1 mentioned above, the affinity of the polar groups and the nitroglycerin is too great, so the skin adhesive partition coefficient of nitroglycerin decreases, and it is not possible to achieve the percutaneous absorption of nitroglycerin at a fixed rate; with the use of method 2, nitroglycerin is decomposed during the crosslinking reaction, and because of the introduction of polar groups, the rate of percutaneous absorption decreases to an unsatisfactory level.

In the pressure-sensitive adhesive layer that contains copolymer and nitroglycerin, the proportion of copolymer is 80–95% by weight, and the proportion of nitroglycerin is 5–20% by weight. Preferably, the proportion of the copolymer is 82–90% by weight, and the proportion of the nitroglycerin is 10–18% by weight. If the proportion of nitroglycerin included is less than 5% by weight, the rate of percutaneous absorption decreases, and in order to achieve a concentration of nitroglycerin in the blood that will give pharmacological effectiveness, it is necessary to use a large surface area of the percutaneous-administration-type pharmaceutical preparation of nitroglycerin. If the proportion of nitroglycerin included is more than 20%, the excess nitroglycerin will bleed out of the pressure-sensitive adhesive layer for the reason that the saturated solubility concentration is less than that. The nitroglycerin that has bled out may give rise to the danger of explosions due to friction and heating of the said preparation and/or impact thereon.

So that the pharmacological effect of nitroglycerin via percutaneous absorption will be obtained continuously for, for example, a 24-hour period, the absorption rate of nitroglycerin through the skin must be uniform at about 2.5–20 mg per patient, and usually 10 mg. So that the needed dose of nitroglycerin can be absorbed through the skin, the amount of nitroglycerin contained in the preparation of this invention should be about 12.5–100 mg, and ordinarily about 50 mg. So that this amount of nitroglycerin will be included, and the thickness of the pressure-sensitive adhesive layer and the surface area of the said preparation of the invention are decided as described below.

The thickness of the pressure-sensitive adhesive layer of the preparation of this invention is 30–200 $\mu$m, and preferably 60–150 $\mu$m. If the thickness of the pressure-sensitive adhesive layer is less than 30 $\mu$m, the adhesive strength is unsatisfactory, so that the preparation will readily come loose from the skin surface during use. Also, it is difficult to prepare a pressure-sensitive adhesive layer with a uniform thickness during manufacture. If the thickness of the pressure-sensitive adhesive layer is more than 200 $\mu$m, then long periods of high temperatures are needed to remove the solvent during manufacture. For that reason, a large amount of the nitroglycerin will volatilize, giving rise to the danger of explosions. The surface area of the preparation depends on the concentration of nitroglycerin in the pressure-sensitive adhesive layer, the thickness of the pressure-sensitive adhesive layer, the intended dose of nitroglycerin, etc. So that the feeling of discomfort at the time of use be small, and to decrease the mechanical skin irritation caused by the pressure-sensitive adhesion of the preparation, it is preferable to keep the surface area of the preparation as small as possible. For that reason, the thickness of the pressure-sensitive adhesive layer is set at a relatively large value within the limits mentioned above, and the concentration of the nitroglycerin is uniformly high. For example, when the thickness of the adhesive material is set at 110 $\mu$m, and about 50 mg of nitroglycerin is included, as mentioned above, then with a concentration of 5% for the nitroglycerin, the surface area of the preparation can be about 90 $cm^2$; with a concentration of 20% for the nitroglycerin, the surface area of the preparation can be about 23 $cm^2$.

For use as the backing of the preparation of this invention, materials that are impermeable to drugs that are ordinarily used as backings for the preparation of this invention can be used, and in particular, films and sheets that have a gas barrier can be used. As materials for the backing, there are, for example, polyester, polyamide, polyvinylidene chloride, polyvinyl chloride, and aluminium. It is also possible to use these substances as sheets or films as backings when laminated with polymers of polyethylene, polypropylene, ethylene-vinylacetate copolymer, etc.

The surface area of the pressure-sensitive adhesive layer of the preparation is protected, where necessary, by paper to be peeled off. As the paper that peels off, there are films made of, for example, polyester, polyvinyl chloride, polyvinylidene chloride, etc; it is possible to use laminated films made of high-quality papers and polyolefin, etc. Ordinarily, so that the paper can be peeled off from the pressure-sensitive adhesive layer, the surface of the paper that comes into contact with the pressure-sensitive adhesive layer is treated with silicone.

The preparation of this invention can be manufactured by the usual coating process using a solution containing base material and nitroglycerin. For example, there is a method in which a solution, in which both the copolymer mentioned above and nitroglycerin are dissolved in an organic solvent, is applied to a backing and dried; and, there is another method in which the said solution is applied to the paper to be peeled off mentioned above and dried, and the resulting pressure-sensitive adhesive layer is made to adhere and transfer to a backing. The proportion of nitroglycerin that can be included in the pressure-sensitive adhesive layer is 5-20% by weight, as described above, but because a few percents of this nitroglycerin volatilize during the manufacturing process, it is preferable to include a slight excess of the amounts mentioned above at the time of manufacture. As the solvent to dissolve the copolymer and nitroglycerin, solvent systems with the solubility parameters of 8.9–9.9 can be used. As such solvents, there are toluene, methyl propionate, dichloroethane, dichloropropane, ethyl acetate, tetrahydrofuran, benzene, chloroform, methyl ethyl ketone, pentachloroethane, methyl acetate, trichloroethane, tetrachloroethane, dichloroethane, acetone, etc. Alternatively, it is possible to use a solvent mixture, with the proviso that the solvent mixture has a solubility parameter within the above limits. In the above solvent system, it is possible to dissolve the copolymer and the nitroglycerin uniformly. Also, when the preparation is being dried, it is possible to remove such a solvent system by the use of relatively low temperatures for relatively short periods of time, so the amount of nitroglycerin that volatilizes can be minimized. If the solvent system has solubility parameters of less than 8.9, then the affinity of the solvent and the copolymer will be strong, and high temperatures for a long period of time will be needed for removal and drying. For that reason, the amount of nitroglycerin that volatilizes increases, which is dangerous. On the other hand, in a polar solvent system with solubility parameters greater than 9.9, it is difficult to dissolve the copolymer uniformly.

The pressure-sensitive adhesive layer formed by the application of solution that contains nitroglycerin and copolymer is usually dried at a temperature from room temperature to around 100° C., so as to minimize the amount of nitroglycerin that volatilizes from the pressure-sensitive adhesive layer.

Antiallergy agents, antioxidants, deodorants, etc., can be further added, if necessary, provided that the release of the nitroglycerin and the adhesiveness of the pressure-sensitive adhesive layer are not damaged.

In the alkyl (meth)acrylate copolymer of the specific composition used in this invention, the amount of nitroglycerin that is needed to reach saturation is about 10–20%; moreover, the copolymer has a suitable degree of affinity for the nitroglycerin. For this reason, it is possible for a large amount of nitroglycerin to be kept in the preparation stably. When the preparation of this invention is used, for a clinically effective dose of nitroglycerin to be absorbed percutaneously, the total amount of nitroglycerin that has been released, for example, 24 hours later, is about 20% or less than the amount of nitroglycerin in the preparation at the beginning. There is not a very great change in the concentration of nitroglycerin between the time immediately after the application of the preparation to the skin and 24 hours later, so the amount of nitroglycerin released (the rate of release) per hour during this time is approximately uniform, with the limits of ±10%. This is supported by the well-known fact that "the rate of release of a drug from a vehicle layer is correlated linearly with the concentration of drug in the vehicle layer." In this way, a preparation can therefore be obtained in which the nitroglycerin is released at a controlled rate and an effective concentration of the drug in the blood is maintained over a long period of time.

The copolymer of alkyl (meth)acrylate has a rolling ball tack value of 2 or less, and can be given a suitable degree of adhesiveness and cohesiveness by being mixed with nitroglycerin. Accordingly, the preparation can be made to adhere to the skin surface for a long period of time. Also, because nitroglycerin is absorbed percutaneously when the preparation is applied for long periods, the adhesive strength of the pressure-sensitive adhesive layer decreases somewhat; this means that the preparation can be removed from the skin without causing pain.

According to the method of this invention, at the time of the manufacture of the preparation, an organic solvent system with a solubility parameter within fixed limits can be used. The affinity of this kind of solvent and the nitroglycerin is weaker than the affinity between the copolymer and the nitroglycerin. For that reason, when the solvent is being dried and removed from the pressure-sensitive adhesive layer that is formed by the coating method, the amount of nitroglycerin that volatilizes can be held to the minimum. Even when this kind of a solvent system is used, substances such as polyisobutylene, natural rubber, polydimethylsiloxane, which have low affinity for nitroglycerin, when used as a base material, increase the volatilization of nitroglycerin at the time of drying, which is hazardous. When a base material with a high affinity to nitroglycerin is used, the release of nitroglycerin when the preparation has been applied to the skin is decreased.

EXAMPLE 1.1

A mixture of 62.1 parts by weight of 2-ethylhexylmethacrylate, 13.3 parts by weight of 2-ethylhexylacrylate, 24.5 parts by weight of dodecylmethacrylate, 0.012 part by weight of hexamethyleneglycol dimethacrylate, and 42 parts by weight of ethyl acetate is prepared. To the mixture, 0.2 part by weight of lauroyl peroxide was added, and a polymerization reaction was carried out by the usual method at 70° C., giving a copolymer of alkyl (meth)acrylates. Then, 100 parts by weight of the ethyl acetate solution that contained the said copolymer (where solid content of this solution is 40%) was mixed with 70.5 parts by weight of an ethyl acetate solution that contained 10% nitroglycerin. This mixture was applied to the surface of paper for being peeled off, and dried, giving a pressure-sensitive adhesive layer 100 μm thick. A laminated film composed of polyethyleneterephthalate and ethylene-vinylacetate copolymer was applied to the surface of the pressure-sensitive adhesive layer, to give a percutaneous-administration-type pharmaceutical preparation of nitroglycerin.

This preparation was evaluated by the methods described below. Also, the rolling ball tack value of the copolymer was measured by the methods of JIS Z-0237. These results are shown in Table 1, which also shows the results of examples 1.2–1.4 and comparative examples 1.1–1.3 below.

Evaluation of application properties: Squares of the preparation described above (2×2 cm) was applied to the chest of a human subject and its peeling off was observed 24 hours later together with the amount of the adhesive left behind when the preparation was peeled off, and evaluated as shown below:

Peeling

| | Area peeled off/area of application |
|---|---|
| None | 2% or less |
| Almost no peeling | 2–10% |
| Peeling | More than 10% |

Amount of adhesive remaining

| | |
|---|---|
| Satisfactory | None remaining |
| Acceptable | Very small amount remaining |
| Poor | Small amount remaining |
| Unacceptable | Remaining all around circumference of applied portion |

EXAMPLE 1.2

The procedure in Example 1.1 was followed except that the monomers used in preparing alkyl (meth)acrylate copolymer were 23.7 parts by weight of 2-ehylhexylacrylate and 76.3 parts by weight of 2-ethylhexylmethacrylate.

EXAMPLE 1.3

The procedure in Example 1.1 was followed except that the monomers used in preparing alkyl (meth)acrylate copolymer were 9.1 parts by weight of 2-ehylhexylacrylate, 78.3 parts by weight of 2-ethylhexylmethacrylate and 12.6 parts by weight of dodecylmethacrylate.

EXAMPLE 1.4

The procedure in Example 1.1 was followed except that the monomers used in preparing alkyl (meth)acrylate copolymer were 18.9 parts by weight of 2-ehylhexylacrylate, 81.1 parts by weight of 2-ethylhexylmethacrylate.

COMPARATIVE EXAMPLE 1.1

The procedure in Example 1.1 was followed, except that the monomers used in preparing alkyl (meth)acrylate copolymer were 68.4 parts by weight of 2-ethylhexylacrylate and 31.6 parts by weight of 2-ethylhexylmethacrylate, and the amount of ethyl acetate solution containing nitroglycerin added was 44.4 parts by weight.

COMPARATIVE EXAMPLE 1.2

The procedure in Example 1.1 was followed, except that the monomers used in preparing alkyl (meth)acrylate copolymer were 17.3 parts by weight of 2-ethylhexylacrylate, 41.5 parts by weight of 2-ethylhexylmethacrylate, and 41.4 parts by weight of dodecylmethacrylate.

COMPARATIVE EXAMPLE 1.3

The procedure in Example 1.1 was followed, except that a polymerization reaction was carried out in which the only polymerization component was 100 parts by weight of 2-ethylhexylmethacrylate.

TABLE 1

| | Composition of copolymers (weight %) | | | Rolling ball tack values of copolymers | Application properties | | Rolling ball tack values of adhesive layer |
|---|---|---|---|---|---|---|---|
| | EHA | EHM | DM | | Peeling | Adhesive remaining | |
| Example 1.1 | 13.3 | 62.1 | 24.5 | <2 | None | Acceptable | 27 |
| Example 1.2 | 23.7 | 76.3 | | <2 | None | Acceptable | 24 |
| Example 1.3 | 9.1 | 78.3 | 12.6 | <2 | None | Satisfactory | 30 |
| Example 1.4 | 18.9 | 81.1 | | <2 | None | Satisfactory | 24 |
| Comparative Example 1.1 | 68.4 | 31.6 | | >32 | None | Unacceptable | >32 |
| Comparative Example 1.2 | 17.3 | 41.5 | 41.4 | >32 | None | Unacceptable | >32 |
| Comparative Example 1.3 | | 100 | | <2 | Peeling | Satisfactory | |

EHA: 2-Ethylhexylacrylate
EHM: 2-Ethylhexylmethacrylate
DM: Dodecylmethacrylate

Table 1 shows that when the base material was a copolymer of alkyl (meth)acrylate containing 2-ethylhexylmethacrylate within the limits of 40–90% by weight, was not pressure-sensitive adhesive in itself with a rolling ball tack value of 2 or less, the adhesiveness of the preparation was satisfactory, and the application properties of the preparation were superior.

EXAMPLE 2

The preparation obtained in Example 1.3 was used in a permeability experiment with the skin of hairless mice and a transferability experiment about nitroglycerin according to the methods described below. The results are shown in Tables 2 and 3.

Experiment for in vitro percutaneous absorption of nitroglycerin through hairless mouse skin: Circles of the preparation were punched out and applied to the skin of the back of hairless mice that had no fur, and these skins were placed in a vessel for skin permeation experiments of the Franz dispersion-cell type. The amount of nitroglycerin that was released into the solution in the cell was measured over time by HPLC. The amount of nitroglycerin was calculated per 25 cm$^2$ of preparation, and the mean for measurements that were repeated three times in this experiment was found.

Experiment on transferability of nitroglycerin: Squares of the preparation (1×1 cm) were applied to the chests of human subjects. The preparation was peeled off after a fixed number of hours, shown in Table 3, and the amount of nitroglycerin remaining in the preparation was measured by HPLC. The decrease in nitroglycerin after the preparation was applied was calculated, and this was considered to be the amount of nitroglycerin transferred by percutaneous administration. The amount of nitroglycerin per 25 cm$^2$ of the preparation was calculated. Ten subjects were used, and their mean values found.

TABLE 2

| Hours applied (hrs.) | 0.5 | 2 | 4 | 6 | 8 | 12 | 16 | 20 | 24 |
|---|---|---|---|---|---|---|---|---|---|

TABLE 2-continued

| Amount of nitroglycerin permeating through skin (mg) | 0.34 | 0.58 | 1.08 | 1.64 | 2.15 | 3.04 | 4.00 | 4.72 | 5.19 |

TABLE 3

| Hours applied (hrs.) | 3 | 8 | 24 |
|---|---|---|---|
| Amount of nitroglycerin transferred (mg) | 1.2 | 2.6 | 7.4 |

Tables 2 and 3 show that the release of nitroglycerin from this preparation was at an approximately uniform rate, and that when applied to the surface of the skin of human subjects, the amount absorbed percutaneously was about 7.4 mg/25 $cm^2$ of the preparation. In this way, it was found that the amount of nitroglycerin absorbed was sufficient.

EXAMPLE 3.1

A mixture of 56 parts by weight of 2-ethylhexylmethacrylate, 44 parts by weight of 2-ethylhexylacrylate, and 67 parts by weight of ethyl acetate. To the mixture, 0.2 part by weight of lauroyl peroxide was added, and a polymerization reaction was carried out by the usual method at 70° C., giving a copolymer of alkyl (meth)acrylates. Then, 100 parts by weight of an ethyl acetate solution that contained the said copolymer (where solid content of this solution is 40%) was mixed with 44.4 parts by weight of an ethyl acetate solution that contained 10% nitroglycerin. This mixture was applied to the surface of paper for being peeled off, and dried, giving a pressure-sensitive adhesive layer 100 μm thick. A laminated film composed of polyethyleneterephthalate and ethylene-vinylacetate copolymer was applied to the surface of the pressure-sensitive adhesive layer, to give a percutaneous-administration-type pharmaceutical preparation of nitroglycerin. The preparation obtained was used for permeability experiments with the skin of hairless mice, and the amount of nitroglycerin that permeated through the skin in 24 hours was found. These results are shown in Table 4, which also shows the results for Examples 3.2 and 3.3 and for Comparative Examples 2.1- 2.3.

EXAMPLE 3.2

The procedure in Example 3.1 was followed except that the monomers used in preparing alkyl (meth)acrylate copolymer were 50 parts by weight of 2-ethylhexylmethacrylate and 50 parts by weight of dodecylmethacrylate.

EXAMPLE 3.3

The procedure in Example 3.1 was followed except that the monomers used in preparing alkyl (meth)acrylate copolymer were 52 parts by weight of 2-ethylhexylmethacrylate, 18 parts by weight of 2-ethylhexylacrylate and 30 parts by weight of dodecylmethacrylate.

COMPARATIVE EXAMPLE 2.1

The procedure in Example 3.1 was followed except that the monomers used in preparing alkyl (meth)acrylate copolymer were 31 parts by weight of 2-ethylhexylmethacrylate, 63 parts by weight of dodecylmethacrylate and 6 parts by weight of butylacrylate.

COMPARATIVE EXAMPLE 2.2

The procedure in Example 3.1 was followed except that the monomers used in preparing alkyl (meth)acrylate copolymer were 86 parts by weight of 2-ethylhexylacrylate and 14 parts by weight of vinyl-pyrrolidone.

COMPARATIVE EXAMPLE 2.3

The procedure in Example 3.1 was followed except that the monomers used in preparing alkyl (meth)acrylate copolymer were 87 parts by weight of butylacrylate and 13 parts by weight of diacetone acrylamide.

TABLE 4

| | Composition of copolymers (wt %) | | | | | Permeation of nitroglycerin through the skins of hairless mice (mg/24 hrs.) |
|---|---|---|---|---|---|---|
| | EHM | EHA | DM | BA | others | |
| Example 3.1 | 56 | 44 | | | | 4.6 |
| Example 3.2 | 50 | | 50 | | | 4.8 |
| Example 3.3 | 52 | 18 | 30 | | | 4.6 |
| Comparative Example 2.1 | 31 | | 63 | 6 | | 3.8 |
| Comparative Example 2.2 | | 86 | | | VP 14 | 1.6 |
| Comparative Example 2.3 | | | | 87 | DAM 13 | 1.2 |

BA: Butyl acrylate
VP: Vinylpyrrolidone
DAM: Diacetone acrylamide

Table 4 shows that when a copolymer of alkyl (meth)acrylate that has alkyl groups with a carbon number of 6 or more is used, the permeation of the skin by nitroglycerin is satisfactory. When a copolymer of butylacrylate which has alkyl groups with the carbon number of 4, was used (Comparative Example 2.1), or when a copolymer that contains monomers with polar groups (Comparative Examples 2.2 and 2.3) was used, the permeability of the nitroglycerin through the skin was decreased.

EXAMPLE 4.1

As in Example 1.1, a preparation was prepared in which the concentration of nitroglycerin in the pressure-sensitive adhesive layer was 10% by weight. The compatibility of the nitroglycerin with this pressure-sensitive adhesive layer of the preparation was observed by eye; also, an experiment on the permeation of nitroglycerin through the skins of hairless mice and the drop hammer test of JIS K-4810 were done. The results are shown in Table 5. The compatibility shown in "Good" in Table 5 means that no bleeding of nitroglycerin from the pressure-sensitive adhesive layer was observed. 60 cm or more in the experiment by the drop hammer test suggests that there is no explosion. Table 5 also shows the results for Examples 4.2 and 4.3 together with those for Comparative Examples 3.1 and 3.2.

EXAMPLE 4.2

As in Example 4.1, a preparation was prepared in which the concentration of nitroglycerin in the pressure-sensitive adhesive layer was 15% by weight.

EXAMPLE 4.3

As in Example 4.1, a preparation was prepared in which the concentration of nitroglycerin in the pressure-sensitive adhesive layer was 20% by weight.

COMPARATIVE EXAMPLE 3.1

As in Example 4.1, a preparation was prepared in which the concentration of nitroglycerin in the pressure-sensitive adhesive layer was 3% by weight.

COMPARATIVE EXAMPLE 3.2

As in Example 4.1, a preparation was prepared in which the concentration of nitroglycerin in the pressure-sensitive adhesive layer was 26% by weight.

TABLE 5

|  | Concentration of nitroglycerin (wt %) | Permeation of nitroglycerin through the skins of hairless mice (mg/24 hrs.) | Experiment by the drop hammer test | Compatibility |
|---|---|---|---|---|
| Comparative Example 3.1 | 3 | 1.1 | more than 60 cm | Good |
| Example 4.1 | 10 | 3.5 | more than 60 cm | Good |
| Example 4.2 | 15 | 5.2 | 40 cm | Good |
| Example 4.3 | 20 | 5.9 | 30 cm | Good or slightly bleeding out |
| Comparative Example 3.2 | 26 | 6.6 | less than 25 cm | Bleeding out partly observed |

Table 5 shows that the release of nitroglycerin from the preparation is reduced when the nitroglycerin concentration is 5% or less. When the concentration of nitroglycerin is 20% or more, the excess nitroglycerin beyond the saturated solubility concentration thereof bleed out of the preparation, which increases the danger of explosions, etc.

EXAMPLE 5.1

As in Example 1.1, the copolymer solution is mixed with 44.4 parts by weight of a 10% nitroglycerin solution in such a manner that nitroglycerin is contained in this mixture in the concentration of 10% by weight. This solution is applied to a paper for being peeled off, and dried for 30 minutes at 60° C., giving a pressure-sensitive adhesive layer 100 μm thick. This layer is covered with a film of polyethylene and polyvinylidene chloride laminated together, resulting in a preparation of this invention. The volatility of nitroglycerin from this preparation and the amount of solvent remaining in the preparation were measured by the methods listed below. The results are shown in Table 6. The results of Examples 5.2-5.3 and of Comparative Example 4 are also shown in Table 6.

Measurement of volatility of nitroglycerin: The preparation was extracted with methanol, and the nitroglycerin in the extract was measured by HPLC. The original amount of nitroglycerin was used as the standard, and the decrease in the amount of nitroglycerin from the above value was calculated, and expressed as a percentage of the original amount of nitroglycerin.

Measurement of amount of solvent remaining: The amount of ethyl acetate (Examples 5.1-5.3) or of cyclohexane (Comparative Example 4) that remained in the pressure-sensitive adhesive layer of the preparation was calculated by gas chromatography, and the concentration thereof in the pressure-sensitive adhesive layer was calculated.

EXAMPLE 5.2

The procedure in Example 5.1 was followed, except that the amount of nitroglycerin solution used was 70.6 parts by weight, so that the amount of nitroglycerin was 15% by weight based on the total weight of the copolymer and nitroglycerin.

EXAMPLE 5.3

The procedure in Example 5.1 was followed except that the amount of nitroglycerin solution used was 100 parts by weight, so that the amount of nitroglycerin was 20% by weight based on the total weight of the copolymer and nitroglycerin.

COMPARATIVE EXAMPLE 4

One hundred parts by weight of natural rubber, 60 parts by weight of terpene resin, 910 parts by weight of cyclohexane, and 177 parts by weight of a 10% solution of nitroglycerin in ethyl acetate were mixed so as to give a homogeneous solution. This was applied to paper for being peeled off, and dried for 30 minutes at 60° C., forming a pressure-sensitive adhesive layer 100 m thick. This was covered with a laminated film of polyethylene and polyvinylidene chloride, to give the preparation. This preparation was tested by the methods of Example 5.1 for the amount of nitroglycerin that volatilizes from the preparation and for the amount of solvent remaining.

TABLE 6

|  | Concentration of nitroglycerin (% by weight) | Volatility of nitroglycerin (%) | Amount of solvent remaining (ppm) |
|---|---|---|---|
| Example 5.1 | 10 | 4.7 | <10 |
| Example 5.2 | 15 | 2.5 | <10 |
| Example 5.3 | 20 | 6.2 | <10 |
| Comparative Example 4 | 10 | 28 | 3000 |

Table 6 shows that when the copolymer of alkyl (meth)acrylate of this invention is used for the preparation, the volatilization of nitroglycerin during the manufacturing process is much less than when a pressure-sensitive adhesive layer of the rubber type is used for the preparation as shown in Comparative Example 4.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A percutaneous pharmaceutical preparation of nitroglycerin comprising a backing that is impervious to medicines, and a pressure-sensitive adhesive layer that is disposed on one surface of said backing, wherein said pressure-sensitive adhesive layer contains alkyl (meth)acrylate copolymer in the concentration of 80-95% by weight and nitroglycerin in the concentration of 5-20% by weight, said copolymer contains as copolymer components 2-ethylhexylmethacrylate in the concentration of 40-90% by weight and alkyl (meth)acrylates with alkyl groups having 6 or more carbon atoms in the concentration of 60-10% by weight based on the total weight of said 2-ethylhexylmethacrylate and said alkyl (meth)acrylates, and said copolymer has a rolling ball tack value of 2 or less.

2. A percutaneous pharmaceutical preparation of nitroglycerin according to claim 1, wherein said alkyl (meth)acrylate copolymer contains poly-functional monomers as copolymer components in the concentration of 0.001-0.1% by weight based on the total weight of all monomers of said copolymer.

3. A percutaneous pharmaceutical preparation of nitroglycerin according to claim 1, wherein said pressure-sensitive adhesive layer contains said (meth)acrylate copolymer in the concentration of 80-90% by weight and nitroglycerin in the concentration of 10-20% by weight.

4. A method for the manufacture of percutaneous pharmaceutical preparations of nitroglycerin comprising: applying an organic-solvent solution that contains alkyl (meth)acrylate copolymer and nitroglycerin to one surface of a backing that is impervious to medicines; and drying said coated layer on the backing, resulting in a pressure-sensitive adhesive layer, wherein said copolymer contains 2-ethylhexylmethacrylate in the concentration of 40-90% by weight and alkyl (meth)acrylates with alkyl groups having 6 or more carbon atoms in the concentration of 60-10% by weight based on the total weight of said 2-ethylhexylmethacrylate and said alkyl (meth)acrylates, and has a rolling ball tack value of 2 or less, said organic solvent has a solubility parameter of 8.9-9.9, and said pressure-sensitive adhesive layer contains said copolymer in the concentration of 80-95% by weight and said nitroglycerin in the concentration of 5-20% by weight.

5. A method for the manufacture of percutaneous pharmaceutical preparations of nitroglycerin according to claim 4, wherein said alkyl (meth)acrylate copolymer contains poly-functional monomers as copolymer components in the concentration of 0.001-0.1% by weight based on the total weight of all monomers of said copolymer.

6. A method for the manufacture of percutaneous pharmaceutical preparations of nitroglycerin according to claim 4, wherein said pressure-sensitive adhesive layer contains said (meth)acrylate copolymer in the concentration of 80-90% by weight and nitroglycerin in the concentration of 10-20% by weight.

* * * * *

UNITED STATES PATENT AND TRADEMARK OFFICE
CERTIFICATE OF CORRECTION

PATENT NO. : 4,971,799
DATED : Nov. 20, 1990
INVENTOR(S) : Takashi Nakagawa et al.

It is certified that error appears in the above-identified patent and that said Letters Patent is hereby corrected as shown below:

At column 13, lines 5-6, please replace the words "60cm or more" with --Use of the term "more than 60cm"--.

At column 14, line 51, please replace the words "100m thick" with --100µm thick--.

Signed and Sealed this

Sixteenth Day of March, 1993

Attest:

STEPHEN G. KUNIN

*Attesting Officer*     Acting Commissioner of Patents and Trademarks